US012630816B2

(12) United States Patent
Shkolnikov et al.

(10) Patent No.: US 12,630,816 B2
(45) Date of Patent: May 19, 2026

(54) ALIGNMENT AND FUSION OF CELLS WITH AN ELECTRICAL FIELD

(71) Applicant: HEWLETT-PACKARD DEVELOPMENT COMPANY, L.P., Spring, TX (US)

(72) Inventors: Viktor Shkolnikov, Palo Alto, CA (US); Alexander Govyadinov, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 1246 days.

(21) Appl. No.: 17/507,152

(22) Filed: Oct. 21, 2021

(65) Prior Publication Data

US 2023/0131266 A1    Apr. 27, 2023

(51) Int. Cl.
| | |
|---|---|
| *C12N 15/02* | (2006.01) |
| *C12M 1/36* | (2006.01) |
| *C12M 1/42* | (2006.01) |
| *C12M 3/06* | (2006.01) |

(52) U.S. Cl.
CPC ............. *C12N 15/02* (2013.01); *C12M 23/16* (2013.01); *C12M 35/02* (2013.01); *C12M 41/48* (2013.01)

(58) Field of Classification Search
CPC ...... C12M 23/16; C12M 41/48; C12M 35/02; C12N 15/02
See application file for complete search history.

(56) References Cited

U.S. PATENT DOCUMENTS

| | | | | |
|---|---|---|---|---|
| 6,540,895 | B1 * | 4/2003 | Spence | ................. G01N 15/14 204/600 |
| 6,632,619 | B1 * | 10/2003 | Harrison | ............... B01L 3/5027 436/805 |
| 6,783,647 | B2 * | 8/2004 | Culbertson | ............ C12N 1/066 204/453 |

(Continued)

FOREIGN PATENT DOCUMENTS

| | | |
|---|---|---|
| WO | WO-2020201206 A1 | 10/2020 |
| WO | WO-2021150631 A1 | 7/2021 |

OTHER PUBLICATIONS

S.C. Bürgel et al. "On-chip electroporation and impedance spectroscopy of single-cells" / Sensors and Actuators B 210 (2015) p. 82-90.

*Primary Examiner* — Shogo Sasaki
(74) *Attorney, Agent, or Firm* — Foley & Lardner LLP

(57) ABSTRACT

A method of alignment and fusion of cells with an electrical field includes firing a first fluid dispenser of an electrofusion device until a first impedance sensor in a first microfluidic channel of the electrofusion device detects a presence of a first cell. The method includes firing a second fluid dispenser of the electrofusion device until a second impedance sensor in a second microfluidic channel of the electrofusion device detects a presence of a second cell. The method includes moving the first cell and the second cell into a merging chamber of the electrofusion device by firing a third fluid dispenser of the electrofusion device, in response to alignment of the first cell in the first microfluidic channel with the second cell in the second microfluidic channel. The method further includes fusing the first cell and the second cell in the merging chamber by creating an electrical field in the merging chamber.

7 Claims, 8 Drawing Sheets

(56)                    References Cited

U.S. PATENT DOCUMENTS

| | | | |
|---|---|---|---|
| 7,091,048 B2 * | 8/2006 | Parce | B01J 19/0093 |
| | | | 436/514 |
| 7,138,269 B2 * | 11/2006 | Blankenstein | B01D 57/02 |
| | | | 436/514 |
| 7,338,796 B1 * | 3/2008 | Davalos | B01L 3/502761 |
| | | | 435/173.6 |
| 7,855,564 B2 | 12/2010 | Sabah et al. | |
| 8,025,853 B2 * | 9/2011 | Numajiri | G01N 35/08 |
| | | | 422/503 |
| 8,765,485 B2 * | 7/2014 | Link | B01F 25/45 |
| | | | 422/503 |
| 10,927,333 B2 | 2/2021 | Zahn et al. | |
| 12,269,035 B2 * | 4/2025 | Kashanin | B01L 3/502715 |
| 2003/0198523 A1 * | 10/2003 | Bohm | F16K 99/0048 |
| | | | 406/198 |
| 2005/0109410 A1 * | 5/2005 | Gilbert | F16K 99/0036 |
| | | | 137/827 |
| 2005/0207940 A1 * | 9/2005 | Butler | B01L 3/502776 |
| | | | 422/403 |
| 2008/0105565 A1 * | 5/2008 | Davalos | B03C 5/005 |
| | | | 204/411 |
| 2008/0213821 A1 * | 9/2008 | Liu | B81C 1/00444 |
| | | | 264/483 |
| 2008/0261295 A1 * | 10/2008 | Butler | C12M 47/04 |
| | | | 436/53 |
| 2009/0029407 A1 * | 1/2009 | Gazit | G01N 27/745 |
| | | | 435/307.1 |
| 2010/0068780 A1 * | 3/2010 | Abonnenc | B03C 5/026 |
| | | | 435/173.6 |
| 2010/0086919 A1 | 4/2010 | McKeon | |
| 2014/0199319 A1 | 7/2014 | Seagal et al. | |
| 2017/0276679 A1 | 9/2017 | Chapman et al. | |
| 2021/0179991 A1 | 6/2021 | Shkolnikov et al. | |

* cited by examiner

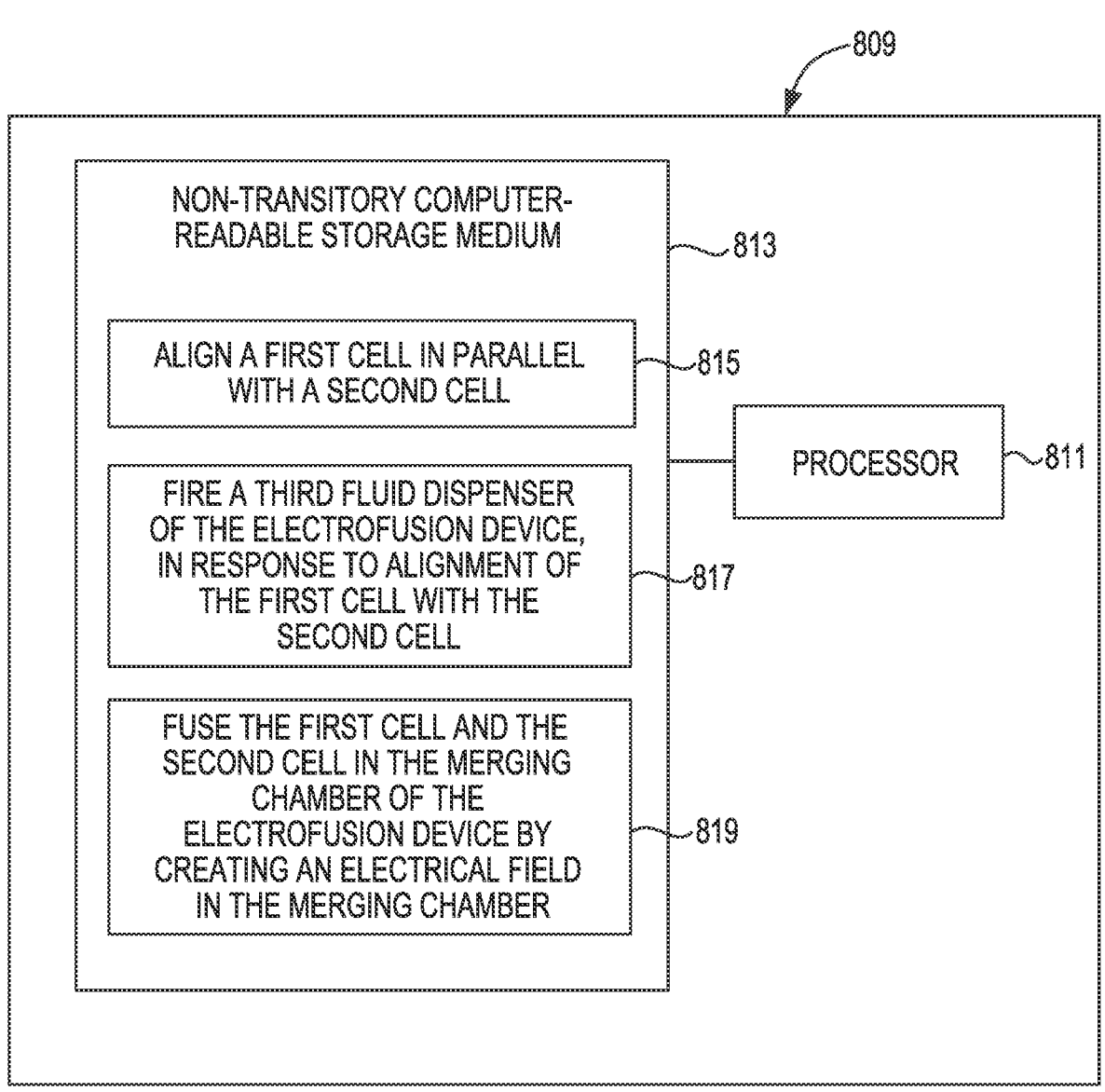

809

NON-TRANSITORY COMPUTER-
READABLE STORAGE MEDIUM

813

ALIGN A FIRST CELL IN PARALLEL
WITH A SECOND CELL

815

FIRE A THIRD FLUID DISPENSER
OF THE ELECTROFUSION DEVICE,
IN RESPONSE TO ALIGNMENT OF
THE FIRST CELL WITH THE
SECOND CELL

817

FUSE THE FIRST CELL AND THE
SECOND CELL IN THE MERGING
CHAMBER OF THE
ELECTROFUSION DEVICE BY
CREATING AN ELECTRICAL FIELD
IN THE MERGING CHAMBER

819

PROCESSOR

ALIGNMENT AND FUSION OF CELLS WITH AN ELECTRICAL FIELD

BACKGROUND

Genetic engineering of living cells and organisms is an important field of research with exciting applications envisaged in medicine, farming, production of animals, production of food and other areas. The momentum in this field has been accelerated by various genome-editing platforms. In these methods, biological material (e.g. deoxyribonucleic acid (DNA), ribonucleic acid (RNA), guide RNA (gRNA), ribonucleoprotein (RNP), protein, virus, etc.) is delivered from the outside of the cell across the cell membrane to the interior of the cell in a process called transfection. In a process referred to as cell fusion, two or more cells combine their plasma membranes to become a single hybrid cell containing DNA from each parent cell. The functional consequence of cell fusion is the formation of a hybrid cell that can maintain genotypic and phenotypic properties of both parent cells. The cell membrane protects the interior of a cell from the introduction of foreign biological material (i.e. transfecting the cell) and therefore transfection and cell fusion include temporarily disrupting this barrier function of the membrane.

There are several ways of disrupting the cell membrane for transfection or cell fusion including using chemical exposure, cell squeezing, mechanical processing of cells in a mix with beads, and electroporation. Electroporation occurs when the living cell is exposed to an external electric field, making the transmembrane potential exceed a threshold value. This leads to the creation of nanoscale pores in the cell membrane, thus making it transiently and reversibly permeable.

BRIEF DESCRIPTION OF THE DRAWINGS

FIG. 8 illustrates an example apparatus for alignment and fusion of cells with an electrical field, in accordance with the present disclosure.

DETAILED DESCRIPTION

Figure 1:
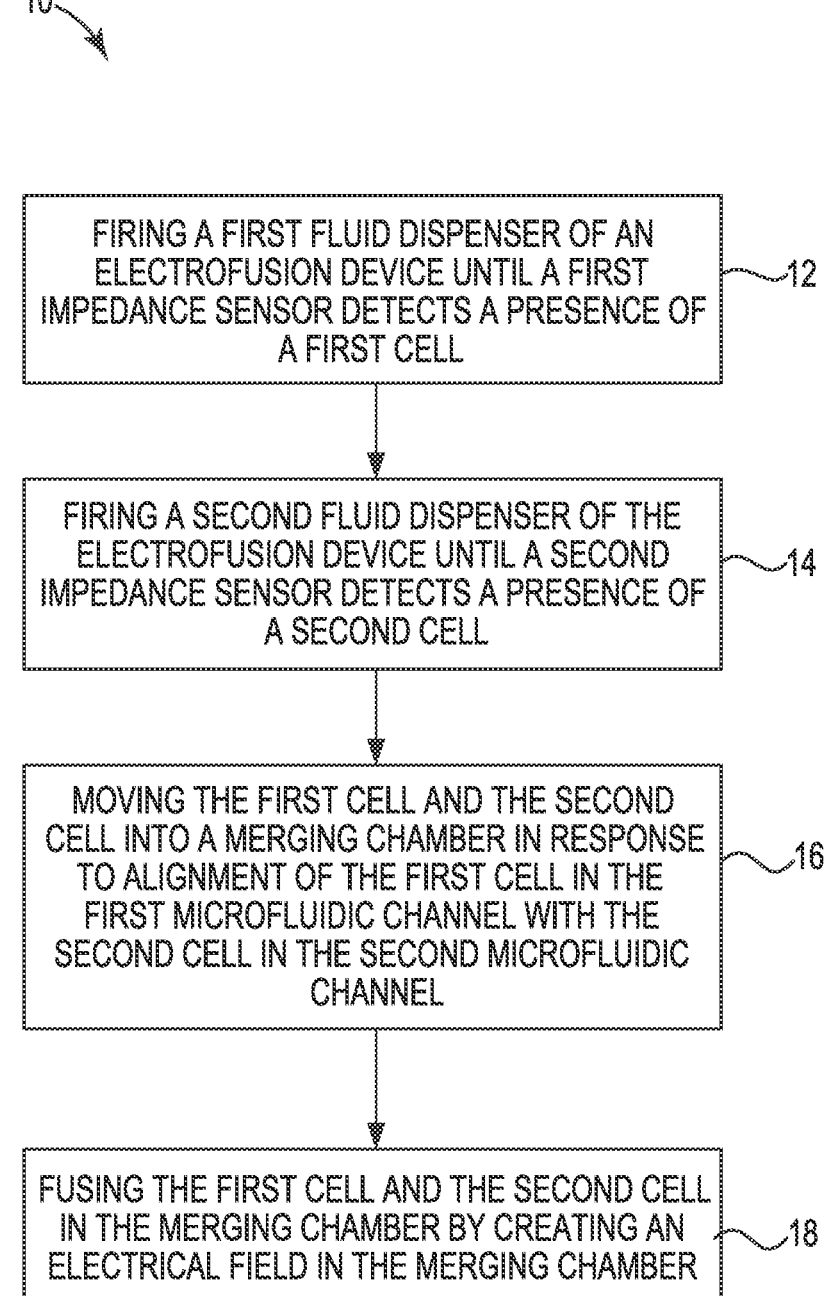
FIG. 1 illustrates an example method for alignment and fusion of cells with an electrical field, in accordance with the present disclosure.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

Therapeutic moieties such as drug compounds are capable of being incorporated into living cells through various processes. Mechanical transformation methods are often complicated and expensive. These methods are often inefficient, and process cells with low throughput. Variations in cell size within a population render mechanical transformation methods difficult to scale up and control in a more automated setting. In addition, controlling vector copy numbers remains a challenge with mechanical devices. A particular type of fused cell includes hybridoma cells. Hybridoma cells are used to produce monoclonal antibodies. Monoclonal antibodies may be used for antigen detection (e.g., ELISA assays, lateral flow assays), and may be used as antibody therapies for a number of conditions including autoimmune disorders and cancer.

Alignment and fusion of cells with an electrical field, in accordance with the present disclosure, results in deliberate and controlled pairing of cells and therefore results in increased fusion efficiency. An example method in accordance with the present disclosure includes firing a first fluid dispenser of an electrofusion device until a first impedance sensor in a first microfluidic channel of the electrofusion device detects a presence of a first cell. The method further includes firing a second fluid dispenser of the electrofusion device until a second impedance sensor in a second microfluidic channel of the electrofusion device detects a presence of a second cell. The method includes moving the first cell and the second cell into a merging chamber of the electrofusion device by firing a third fluid dispenser of the electrofusion device, in response to alignment of the first cell in the first microfluidic channel with the second cell in the second microfluidic channel. The method also includes fusing the first cell and the second cell in the merging chamber by creating an electrical field in the merging chamber.

In some examples, the method includes detecting placement of the first cell in the first microfluidic channel using a first impedance sensor, and detecting placement of the second cell in the second microfluidic channel using a second impedance sensor. In some examples, the method includes aligning the first cell in the first microfluidic channel parallel with the second cell in the second microfluidic channel by selectively firing the first fluid dispenser, the second fluid dispenser, or combinations thereof. In some examples, the method includes dispensing the fused cell from the electrofusion device by firing the third fluid dispenser. In some examples, the method includes aligning the first cell in the first microfluidic channel with the second cell in the second microfluidic channel by adjusting a firing rate of the first fluid dispenser or the second fluid dispenser.

A non-limiting example apparatus in accordance with the present disclosure includes a pairing region, a non-transitory computer readable medium, and a merging chamber. In such an example, the pairing region includes a first microfluidic channel including a first impedance sensor, wherein the first microfluidic channel is in fluidic communication with a first fluid dispenser. The pairing region also includes a second microfluidic channel including a second impedance sensor, wherein the second microfluidic channel is in fluidic communication with a second fluid dispenser. The non-transitory computer readable medium stores instructions that, when executed, cause the first fluid dispenser and the second fluid dispenser to align a first cell in the first microfluidic channel and a second cell in the second microfluidic channel by actuating the first fluid dispenser and the second fluid dispenser. In various examples, the merging chamber is in fluid communication with the first microfluidic channel and the second microfluidic channel, wherein the merging chamber comprises a plurality of electrodes to fuse the first cell with the second cell in response to alignment of the first cell in the first microfluidic channel with the second cell in the second microfluidic channel.

In some examples, the non-transitory computer readable medium includes instructions that, when executed, cause the first fluid dispenser to actuate until the first impedance sensor detects the first cell in the first microfluidic channel, and the second fluid dispenser to actuate until the second impedance sensor detects the second cell in the second microfluidic channel. In some examples, the non-transitory computer readable medium includes instructions that, when executed, cause the first fluid dispenser to actuate at a reduced rate responsive to the first impedance sensor detecting the first cell in the first microfluidic channel. In some examples, the first microfluidic channel and the second microfluidic channel are disposed in series with the merging chamber, and the first microfluidic channel and the second microfluidic channel are disposed in parallel. In some examples, the apparatus includes a third fluid dispenser, and the non-transitory computer readable medium includes instructions that, when executed, cause the third fluid dispenser to actuate in response to alignment of the first cell in the first microfluidic channel with the second cell in the second microfluidic channel. In some examples, the first fluid dispenser and the second fluid dispenser include resistors. In some examples, the first impedance sensor is disposed upstream from a first junction between the first microfluidic channel and the first fluid dispenser, and the second impedance sensor is disposed upstream from a second junction between the second microfluidic channel and the second fluid dispenser. In some examples, the apparatus includes a third impedance sensor disposed downstream from the first junction and a fourth impedance sensor disposed downstream from the second junction, wherein the third impedance sensor and the fourth impedance sensor are disposed upstream from the merging chamber.

Another non-limiting example apparatus in accordance with the present disclosure includes a non-transitory computer readable medium storing instructions that, when executed, cause a processor to align a first cell in a first microfluidic channel of an electrofusion device in parallel with a second cell in a second microfluidic channel of the electrofusion device by firing a first fluid dispenser in the first microfluidic channel and a second fluid dispenser in the second microfluidic channel. The non-transitory computer readable medium also stores instructions that, when executed, cause the processor to fire a third fluid dispenser of the electrofusion device, in response to alignment of the first cell with the second cell in a merging chamber of the electrofusion device. Yet further, the non-transitory computer readable medium stores instructions that, when executed, cause the processor to fuse the first cell and the second cell in the merging chamber of the electrofusion device by creating an electrical field in the merging chamber.

In some examples, the instructions to align the first cell in the first microfluidic channel with the second cell in the second microfluidic channel, include instructions that, when executed, cause the processor to change a firing rate of the first fluid dispenser in response to receipt of a first signal from a first impedance sensor in the first microfluidic channel indicative of the presence of the first cell, and stop firing the first fluid dispenser and the second fluid dispenser in response to receipt of a second signal from a second impedance sensor indicative of the presence of the second cell in the second microfluidic channel.

Turning now to the figures, FIG. 1 illustrates an example method 10 for alignment and fusion of cells with an electrical field, in accordance with the present disclosure. At 12, the method 10 includes firing a first fluid dispenser of an electrofusion device until a first impedance sensor in a first microfluidic channel of the electrofusion device detects a presence of a first cell. As used herein, an electrofusion device refers to or includes a microfluidic device including circuitry and capable of electroporation of cells. A microfluidic device may enable manipulation and control of small volumes of fluid through microfluidic fluidic channels. For example, a microfluidic device may enable manipulation and/or control of volumes of fluid on the order of microliters (i.e., symbolized pL and representing units of $10^6$ liter), nanoliters (i.e., symbolized nL and representing units of $10^9$ liter), picoliters (i.e., symbolized pL and representing units of $10^{12}$ liter) or femtoliters (i.e., symbolized fL and representing units of $10^{15}$ liter).

The electrofusion device may include an impedance sensor or a plurality of impedance sensors capable of detecting presence of a cell. As used herein, an impedance sensor refers to or includes a sensing material fabricated on electrodes, which is capable of measuring the change in impedance of a sensor while applying a sinusoidal voltage. Living cells are surrounded by an outer cell membrane that restricts the movement of ions and solutes between the cell interior and the exterior of the cell. Impedance sensors apply a small alternating current (AC) electrical signal to probe the value of the impedance of sensor electrodes immersed in a conductive medium. Living cells can alter the electric field between electrodes causing a change in the electrical impedance that can be detected by the sensor electrodes. The measurement of impedance by the sensor can reflect the electrophysiological state of the cell and can allow the biophysical properties of the cell to be monitored.

An impedance sensor may form an electric field region within microfluidic channels of the electrofusion device. The impedance sensor may include a local electrical ground and an electrode which cooperate to form a region of electric field lines that extend within the microfluidic channel. When a cell passes through the electric field region, the electric field lines of the region are at least partially obstructed by the cell such that the electric field lines of the region are altered and travel around the cell. The increased length of the electric field lines, resulting from having to travel around the cell, increases or raises the electrical impedance that may be detected at the electrode. As a result, the increase in impedance resulting from obstruction of the electric field region by the cell serves as an indicator of one or more characteristics of the cell, such as the size of the cell.

As used herein, a fluid dispenser refers to or includes a firing chamber to receive a fluid, such as from a manifold, fluid slot, or fluid hole array. In various examples, a carrier fluid may be ejected by droplet from the fluid dispenser via a pulse of current that is passed through an ejector in the form of a heater positioned in the fluid dispenser. Heat from the heater causes a rapid vaporization of the carrier fluid in the fluid dispenser to form a drive bubble, which causes a large pressure increase that propels a droplet of carrier fluid into the electrofusion device. In some examples, the fluid dispenser can be designed to dispense carrier fluid into the electrofusion device via a piezoelectric process. In such piezoelectric processes, a voltage may be applied to the ejector in the form of a piezoelectric material located in the fluid dispenser. When a voltage is applied, the piezoelectric material changes shape, which generates a pressure pulse that forces a droplet of carrier fluid from the fluid dispenser into the electrofusion device. It is appreciated that other forms of ejector can be used in accordance with the present disclosure.

At 14, the method 10 includes firing a second fluid dispenser of the electrofusion device until a second impedance sensor in a second microfluidic channel of the electrofusion device detects a presence of a second cell. Throughout this disclosure, use of the terms "first" and "second" does not import a temporal distinction, and is instead used to distinguish one object from another object of the same type.

At 16, the method 10 includes moving the first cell and the second cell into a merging chamber of the electrofusion device by firing a third fluid dispenser of the electrofusion device, in response to alignment of the first cell in the first microfluidic channel with the second cell in the second microfluidic channel. As used herein, a merging chamber refers to or includes a portion of the electrofusion device including electrodes. The electrodes may comprise members formed from electrically conductive material, such as an electrically conductive metal, which cooperate to apply an electrostatic field across the interior of the merging chamber upon being electrically charged. The electrodes may be electrically isolated from one another so as to form an electrical field through the contents of merging chamber. The merging chamber may apply the electrical field to the contents of the merging chamber when the first cell and the second cell are aligned. As used herein, two cells are aligned if they are disposed parallel to one another along a same plane such that a first cell does not extend in front of or behind the second cell by greater than half of the width of the cell.

In some examples, the method 10 includes aligning the first cell in the first microfluidic channel parallel with the second cell in the second microfluidic channel by selectively firing the first fluid dispenser, the second fluid dispenser, or combinations thereof. As discussed further herein, cells may be moved through the electrofusion device by ejecting carrier fluid from one fluid dispenser or from both fluid dispensers. Put another way, a voltage may be applied to the ejector in one of the fluid dispensers, or a voltage may be applied to the ejector in both of the fluid dispensers so as to move a cell or both cells through the electrofusion device.

At 18, the method 10 includes fusing the first cell and the second cell in the merging chamber by creating an electrical field in the merging chamber. For instance, as the first cell and the second cell enter the merging chamber, an electric field formed by the electrodes may porate the cells. Because of the alignment of the cells in the merging chamber (e.g., because the cells are aligned parallel to one another in the merging chamber), the proximity of the cells to one another facilitates fusion.

As discussed more thoroughly herein, the method 10 includes detecting placement of the first cell in the first microfluidic channel using a first impedance sensor, and detecting placement of the second cell in the second microfluidic channel using a second impedance sensor. As such, the method 10 may include aligning the first cell in the first microfluidic channel parallel with the second cell in the second microfluidic channel by selectively firing the first fluid dispenser, the second fluid dispenser, or combinations thereof. Thereafter, the method 10 may include dispensing the fused cell from the electrofusion device by firing the third fluid dispenser. In such a manner, a fused cell (also referred to as a transfected cell) may be ejected from the electrofusion device.

Various types of cells may be fused using the apparatus and method described in the present disclosure. For instance, alignment and fusion of cells with an electrical field, in accordance with the present disclosure, may allow for production of hybridoma cells. A hybridoma refers to a hybrid cell produced by the fusion of an antibody-producing lymphocyte (such as a B-cell) with a tumor cell (such as a myeloma cell). Producing a hybridoma often involves bringing B-lymphocyte cells together with myeloma cells in a solution containing polyethylene glycol (PEG). This method does not use microfluidic structures or electric fields. However, PEG is somewhat cytotoxic and so many of the fused cells die, wasting precious B-cells, and reducing the pool of antibodies that can be produced. Additionally, non-specific membrane fusion occurs, again wasting precious B-cells, and reducing the pool of antibodies that can be produced. In order to bypass the cytotoxicity of PEG, fusogenic viruses such as Sedai virus and vesicular stomatitis virus can be used. However, fusion of cells using fusogenic viruses can also be non-specific, and careful purification and quality assurance is used to ensure that the resultant antibody product is free from virus. Lastly, electrical field fusion via electroporation has been used for cell fusion for hybridoma production. In bulk electrofusion, a mixture of B-cells and myeloma are loaded in cuvettes with parallel plate electrodes, and an electric field is applied. The electric field initially induces the cells to form "pearl chains", and then briefly breaks down the cell membrane forming pores. Once the field is turned off, the cells that were touching each other fuse their membranes together. This bulk electrofusion has an advantage over the use of PEG and fusogenic viruses in that it does not use reagents to be cleaned up after the cell fusion processes. However, like PEG-based and fusogenic virus-based methods, bulk electrofusion methods are non-specific and so waste precious B-cells, which results in a reduction of the pool of antibodies that can be produced. Non-specific cellular fusion results in some of the B-cells being fused to myeloma cells to form a functional hybridoma, while other B-cells are fused to each other and/or other cell constructs. Different and/or additional cellular fusions are possible, which results in combinations of cellular material other than the desired myeloma and B-cell fusion. Such non-specific fusion wastes precious B-cells, and reduces the overall pool of antibodies that are possible. Alignment and fusion of cells with an electrical field, in accordance with the present disclosure, results in deliberate and controlled pairing of cells. By aligning cells within an electrofusion device, as described herein, a higher production of viable hybridomas may be achieved. Moreover, by enabling detection and alignment of individual cells, aspects of the present disclosure allow for high throughput of fused cells, such as hybridomas. In various examples described herein, alignment of cells to be fused and ejection of the fused cell may be controlled by selective dispense firing of fluid dispensers. For instance, the above described method may include aligning the first cell in the first microfluidic channel with the second cell in the second microfluidic channel by adjusting a firing rate of the first fluid dispenser or the second fluid dispenser. A higher firing rate of a fluid dispenser may result in a greater volume of fluid dispensed therefrom, and a lower firing rate of the fluid dispenser may result in a lower volume of fluid dispensed therefrom. As a result, to increase a rate of flow within a channel, a higher firing rate may be used whereas to decrease a rate of flow within the channel, a lower firing rate may be used.

Figure 2:
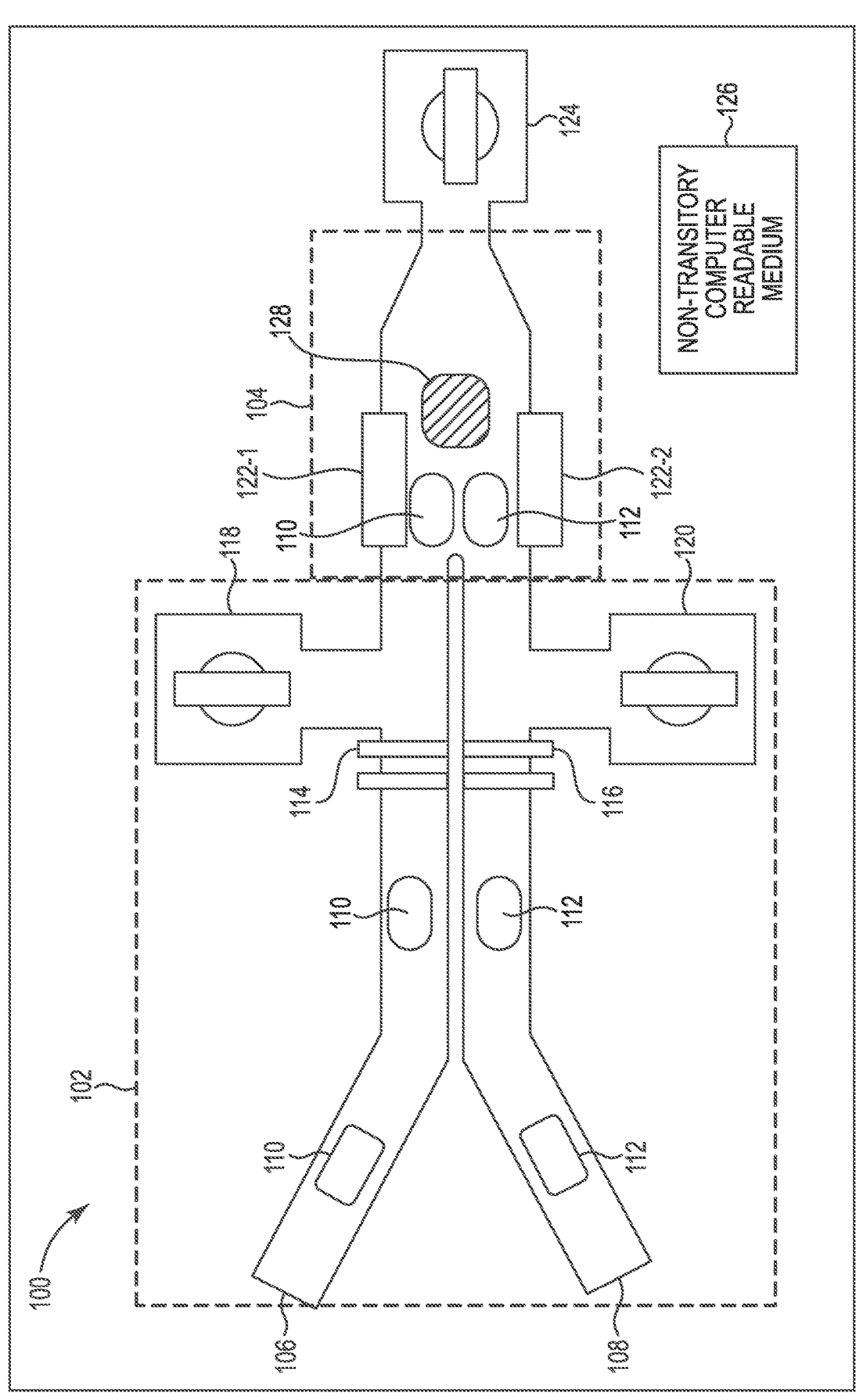
FIG. 2 illustrates an example apparatus, in accordance with the present disclosure.

FIG. 2 illustrates an example apparatus 100, in accordance with the present disclosure. As illustrated in FIG. 2, the apparatus 100 may include a pairing region 102. The pairing region may include a first microfluidic channel including a first impedance sensor, wherein the first microfluidic channel is in fluidic communication with a first fluid dispenser. For instance, the pairing region 102 may include a first microfluidic channel 106 including a first impedance sensor 114, wherein the first microfluidic channel 106 is in fluidic communication with a first fluid dispenser 118 to move a first cell 110 through the first microfluidic channel 106. The pairing region may also include a second microfluidic channel including a second impedance sensor, wherein the second microfluidic channel is in fluidic communication with a second fluid dispenser. For instance, the pairing region 102 may include a second microfluidic channel 108 including a second impedance sensor 116, wherein the second microfluidic channel 108 is in fluidic communication with a second fluid dispenser 120 to move a second cell 112 through the second microfluidic channel 108. In some examples, the first fluid dispenser and the second fluid dispenser include resistors.

The apparatus 100 may also include a non-transitory computer readable medium storing instructions that, when executed, cause the apparatus 100 to perform various operations. As such, the apparatus 100 may include, or be coupled to, a processor (not illustrated) capable of executing the instructions stored in the non-transitory computer readable medium 126. The processor may be a central processing unit (CPU), a semiconductor-based microprocessor, and/or other hardware device suitable to control operations of the apparatus 100. The computer-readable storage medium 126 may be an electronic, magnetic, optical, or other physical storage device that contains or stores executable instructions. Thus, computer-readable storage medium 126 may be, for example, Random Access Memory (RAM), an Electrically Erasable Programmable Read-Only Memory (EEPROM), a storage device, an optical disc, etc. In some examples, the computer-readable storage medium 126 may be a non-transitory storage medium, where the term 'non-transitory' does not encompass transitory propagating signals. The computer-readable storage medium 126 may be encoded with a series of executable instructions as discussed more thoroughly below.

The computer-readable storage medium 126 may store instructions that, when executed cause the first fluid dispenser 118 and the second fluid dispenser 120 to align a first cell 110 in the first microfluidic channel 106 and a second cell 112 in the second microfluidic channel 108 by actuating the first fluid dispenser 118 and the second fluid dispenser 120. In some examples, the non-transitory computer readable medium 126 includes instructions that, when executed, cause the first fluid dispenser 118 to actuate until the first impedance sensor 114 detects the first cell 110 in the first microfluidic channel 106, and the second fluid dispenser 120 to actuate until the second impedance sensor 116 detects the second cell 112 in the second microfluidic channel 108. In some examples, the non-transitory computer readable medium 126 includes instructions that, when executed, cause the first fluid dispenser 118 to actuate at a reduced rate responsive to the first impedance sensor 114 detecting the first cell 110 in the first microfluidic channel 106.

The apparatus 100 may also include a merging chamber. For instance, the apparatus 100 may include a merging chamber 104 in fluid communication with the first microfluidic channel 106 and the second microfluidic channel 108. In various examples, the merging chamber 104 comprises a plurality of electrodes 122-1 and 122-2 to fuse the first cell 110 with the second cell 112 in response to alignment of the first cell 110 in the first microfluidic channel 106 with the second cell 112 in the second microfluidic channel 108. The resultant cell 128 includes material from the first cell 110 and the second cell 112. For instance, in examples in which the first cell 110 is a B-cell and the second cell 112 is a myeloma cell, the cell 128 is a hybridoma cell.

In some examples, the first microfluidic channel 106 and the second microfluidic channel 108 are disposed in series with the merging chamber 104, and the first microfluidic channel 106 and the second microfluidic channel 108 are disposed in parallel. As used herein, the term "in series" refers to or includes microfluidic channels that are connected end-to-end in a line to form a path for fluid to flow. As used herein, the term "in parallel" refers to or includes microfluidic channels that are to a same input. While microfluidic channels in parallel may be disposed parallel to one another, microfluidic channels may be disposed alongside one another at an angle. A non-limiting example of an apparatus including microfluidic channels in parallel and disposed at an angle relative to one another is provided at least in FIG. 2.

As illustrated in FIG. 2, the apparatus 100 includes a third fluid dispenser 124. In various examples, the non-transitory computer readable medium 126 includes instructions that, when executed, cause the third fluid dispenser 124 to actuate in response to alignment of the first cell 110 in the first microfluidic channel 106 with the second cell 112 in the second microfluidic channel 108. In such a manner, once the first cell 110 is aligned with the second cell 112, both cells may move toward the third fluid dispenser 124 together, as illustrated in FIG. 2.

During operation, the first fluid dispenser 119 may be fired until the impedance sensor 114 detects a presence of a cell (such as cell 110) above it, and then the firing of the impedance sensor 114 is stopped, thereby halting the cell 110 above the sensor 114. Similarly, second fluid dispenser 120 is fired until the second impedance sensor 116 detects the presence of a cell above it, such as cell 112, and then the firing of the second fluid dispense 120 is stopped, thereby halting the cell 112 above the sensor 116. These two dispensers and detectors may work in parallel. Once in their respective positions, the third fluid dispenser 124 may fire, moving the two cells 110 and 112 together into the merging chamber 104. Once in the merging chamber 104, the electrodes 122-1 and 122-2 may be pulsed, so as to porate and fuse the cells 110 and 112, creating a fused cell 128 (such as a hybridoma). The third dispenser 124 may then be fired again to move the fused cell 128 and dispense it out of the apparatus 100. The fused cell 128 may then be dispensed into a specific well of a microwell plate or other apparatus. The cells in the wells may be cultured, generating a monoculture of cells in each well. Thus, each well may produce a specific antibody, which can then be interrogated and selected for.

Figure 3:
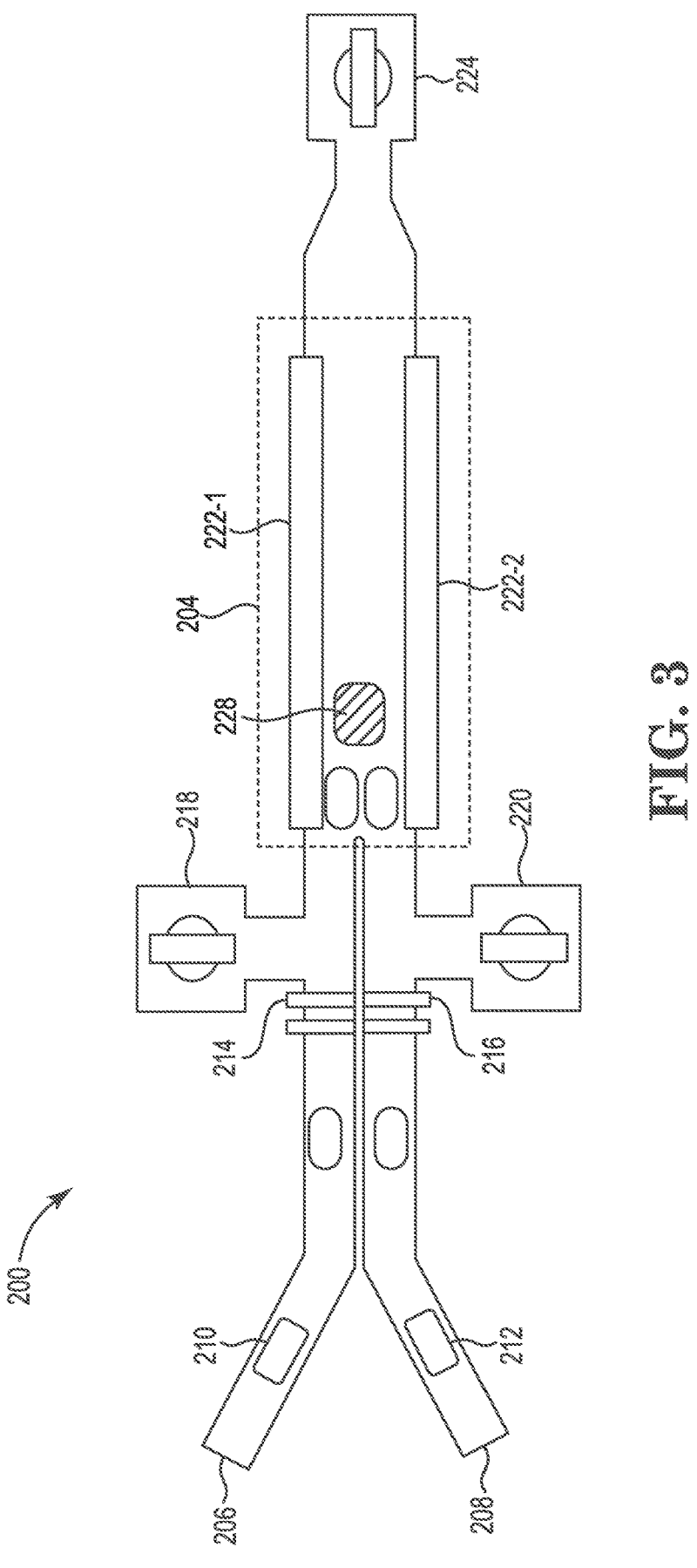
FIG. 3 illustrates an example apparatus including an elongated merging chamber, in accordance with the present disclosure.

FIG. 3 illustrates an example apparatus 200 including an elongated merging chamber, in accordance with the present disclosure. In general, the apparatus 200 shown in FIG. 3 may include various components that are the same and/or substantially similar to the apparatus 100 shown in FIG. 2, which was described in greater detail above. As such, for brevity and ease of description, various details relating to certain components in the apparatus 200 shown in FIG. 3 may be omitted herein to the extent that the same or similar details have already been provided above. For instance, while impedance sensors 214 and 216, and fluid dispensers 218 and 220, are illustrated, details relating to the impedance sensors 214 and 216 and fluid dispensers 218 and 220 are not discussed with regards to FIG. 3.

As illustrated in FIG. 3, the first microfluidic channel 206 and the second microfluidic channel 208 are disposed in parallel, and both the first microfluidic channel 206 and the second microfluidic channel 208 are disposed in series with the merging chamber 204. In the example illustrated in FIG. 3, the merging chamber 204 comprises a plurality of electrodes 222-1 and 222-2 which have a greater length extending a length of the merging chamber as compared to the apparatus 100 illustrated in FIG. 2. For instance, as the first cell 210 and the second cell 212 travel through the merging chamber 204, an electrical field generated by electrode 222-1 and electrode 222-2 may fuse the first cell 210 and the second cell 212 to form cell 228. As discussed with reference to FIG. 2, dispenser 224 may eject the fused cell 228.

In operation, the first fluid dispenser 218 may be fired until the first impedance sensor 214 detects a presence of a cell 210 above it, and then the first impedance sensor 214 stops firing, thereby halting the cell 210 above the sensor 214. Similarly, the second fluid dispenser 220 is fired until the second impedance sensor 216 detects the presence of a cell 212 above it and then firing of the second fluid dispenser 220 is stopped, thereby halting the cell 212 above the sensor 216. These two dispensers and detectors may work in parallel. Once in their respective positions, the third fluid dispenser 224 fires, moving the two cells 210 and 212 together into the merging chamber 204. In the merging chamber 204, the electrodes 222-1 and 222-2 may be continuously on, with an alternating current electric field. When the cells 210 and 212 enter the merging chamber 204, the cells 210 and 212 are porated, and when the cells 210 and 212 leave the electric field, the cells 210 and 212 fuse creating a fused cell 228. Then, the third fluid dispenser may be fired to move the fused cell 228 through the merging chamber 204 and dispense the fused cell 228 out of the microfluidic device 200. The fused cell 228 may then be dispensed into a specific well of a multiwall plate or other vessel. The cells in the multiwall plate may be cultured, thereby generating a monoculture of cells in each well. Thus, each well may produce a specific antibody, which can then be interrogated and selected for.

Figure 4:
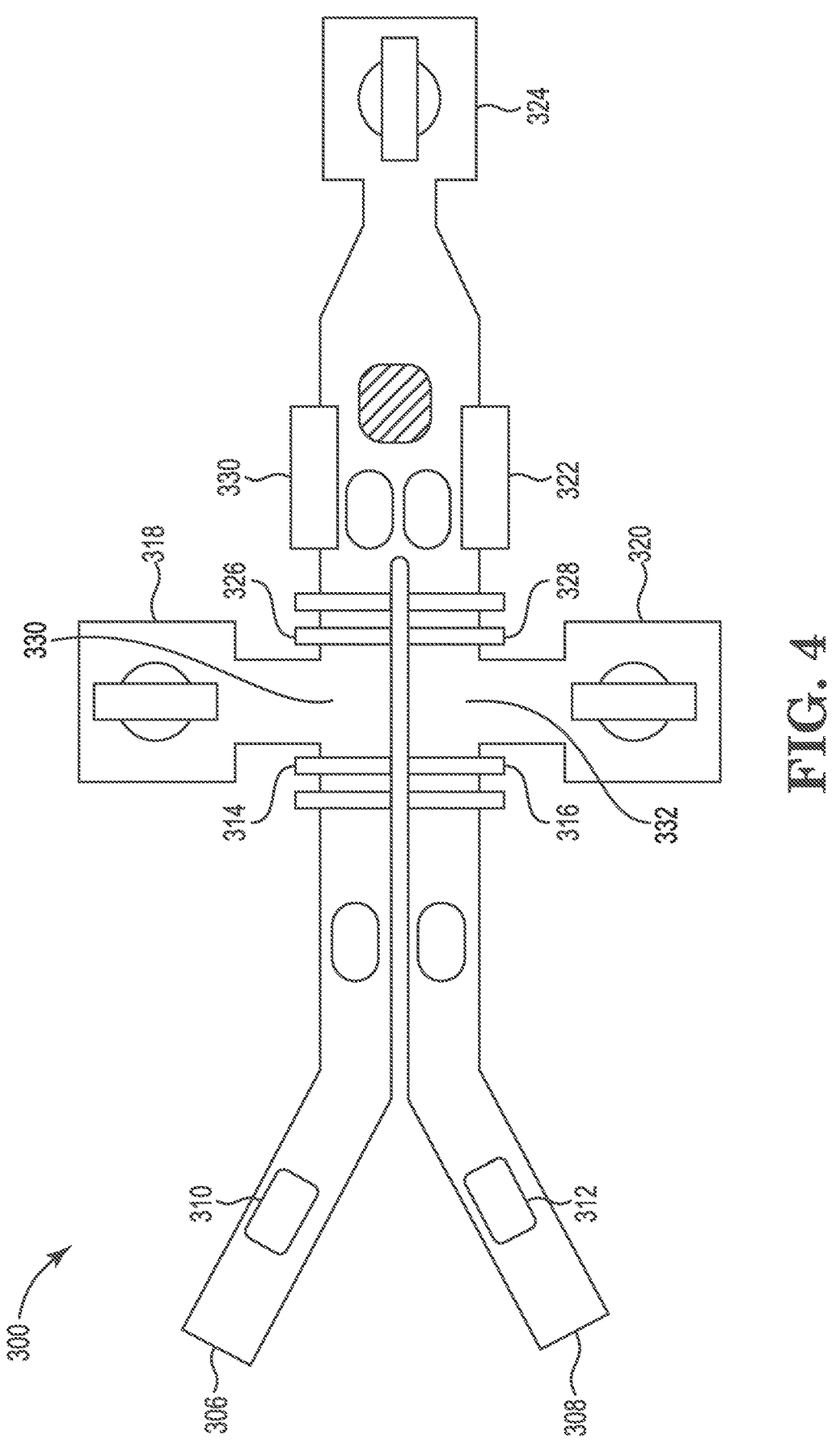
FIG. 4 illustrates an example apparatus including a second set of impedance sensors, in accordance with the present disclosure.

FIG. 4 illustrates an example apparatus 300 including a second set of impedance sensors, in accordance with the present disclosure. In general, the apparatus 300 shown in FIG. 4 may include various components that are the same and/or substantially similar to the apparatus 100 shown in FIG. 2, which was described in greater detail above. As such, for brevity and ease of description, various details relating to certain components in the apparatus 300 shown in FIG. 4 may be omitted herein to the extent that the same or similar details have already been provided above in relation to the apparatus 100 illustrated in FIG. 2. For instance, while cells 310 and 312, electrodes 330 and 322, and dispenser 324 are illustrated in FIG. 4, details relating to cells 310 and 312, electrodes 330 and 322, and dispenser 324, are not provided with reference to FIG. 4.

As illustrated in FIG. 4, a first set of impedance sensors, 314 and 316 may be disposed on a first side of the fluid dispensers and a second set of impedance sensors, 326 and 328, may be disposed on a second side of the fluid dispensers. In other words, referring to the first microfluidic channel 306, the first impedance sensor 314 is disposed upstream from a first junction 330 between the first microfluidic channel 306 and the first fluid dispenser 318, and the second impedance sensor 326 is disposed downstream from the first junction 330 between the first microfluidic channel 306 and the first fluid dispenser 318. Similarly, referring to the second microfluidic channel 308, the first impedance sensor 316 is disposed upstream from a second junction 332 between the second microfluidic channel 308 and the second fluid dispenser 320, and the second impedance sensor 328 is disposed downstream from the second junction 332 between the second microfluidic channel 308 and the second fluid dispenser 320. The secondary impedance detectors, 326 and 328 may detect if the cells have moved into the merging chamber. Put another way, the apparatus 300 may include a third impedance sensor disposed downstream from the first junction and a fourth impedance sensor disposed downstream from the second junction, wherein the third impedance sensor and the fourth impedance sensor are disposed upstream from the merging chamber. Although various figures illustrate an impedance sensor comprising two electrodes each, examples are not so limited. In some examples, an array of electrodes (3 or more) may be used to obtain cell position. Various other arrangements of an apparatus for alignment and fusion of cells with an electrical field are contemplated, such as the apparatus illustrated in FIG. 5.

Figure 5:
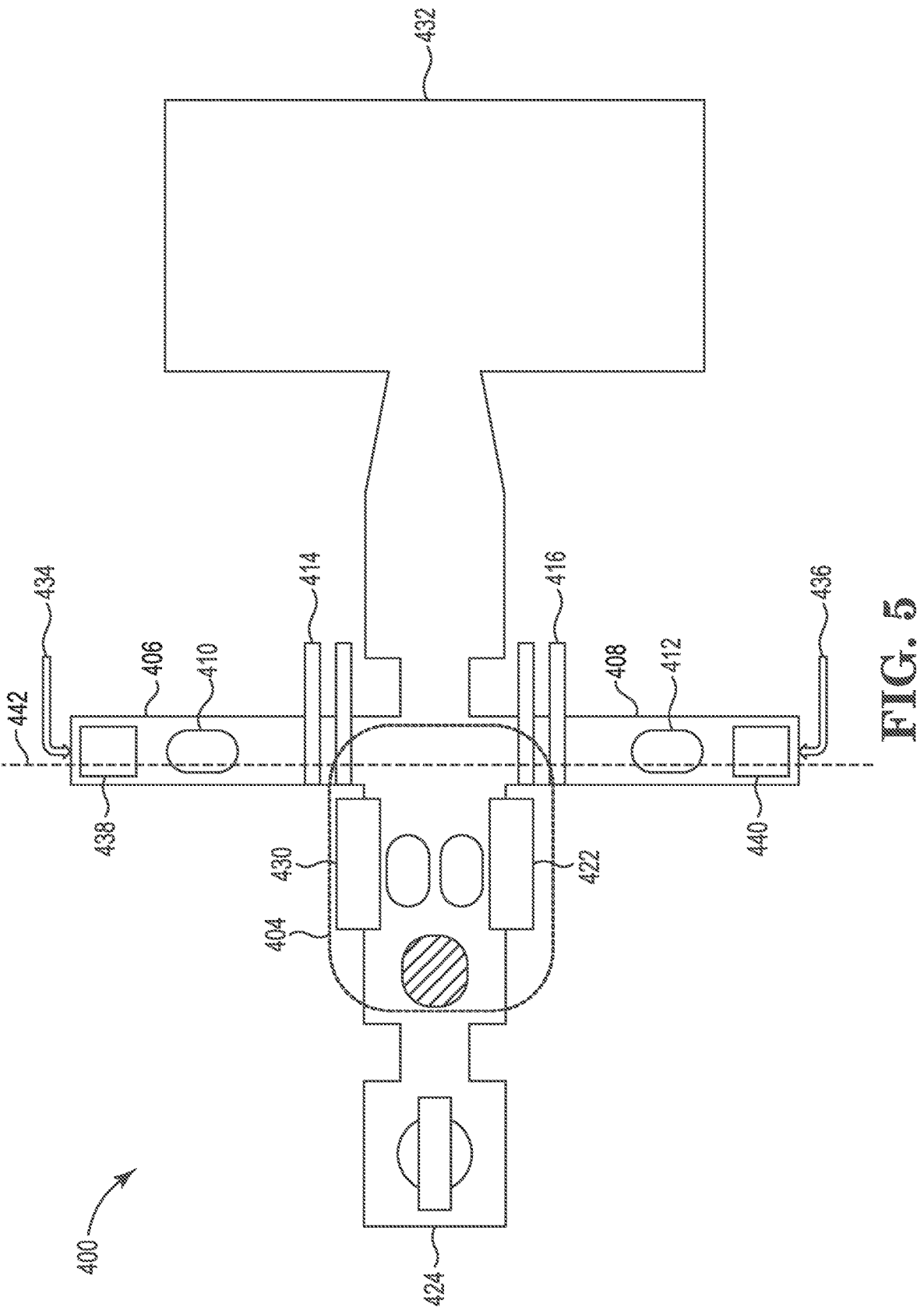
FIG. 5 illustrates an example apparatus with an orthogonal orientation, in accordance with the present disclosure.

FIG. 5 illustrates an example apparatus 400 with an orthogonal orientation, in accordance with the present disclosure. In general, the apparatus 400 shown in FIG. 5 may include various components that are the same and/or substantially similar to the apparatus 100 shown in FIG. 2, which was described in greater detail above. As such, for brevity and ease of description, various details relating to certain components in the apparatus 400 shown in FIG. 5 may be omitted herein to the extent that the same or similar details have already been provided above in relation to the apparatus 100 illustrated in FIG. 2.

As illustrated by the example apparatus 400, in some examples the first microfluidic channel and the second microfluidic channel are disposed in series along a plane 442, and the merging chamber 404 is disposed orthogonal to the plane 442. For instance, the first microfluidic channel 406 and the second microfluidic channel 408 are disposed in series along plane 442 and orthogonal to the merging chamber 404. Similar to the apparatus 300 illustrated in FIG. 4, the merging chamber 404 may include electrodes 430 and 422.

The apparatus 400 may also include a first push pump 438 and a second push pump 440. Each of push pump 438 and push pump 440 may drive fluid from fluid reservoirs 434 and 436, respectively, with cells through the first microfluidic channel 406 and the second microfluidic channel 408. Similar to the example apparatus 100 illustrated in FIG. 2, a first impedance sensor 414 may be disposed in the first microfluidic channel 406 and a second impedance sensor 412 may be disposed in the second microfluidic channel 408.

In operation, a first push pump 438 and with the same frequency of a second push pump 440 is fired until either a first cell 410 is detected by a first impedance sensor 414 or a second cell 412 is detected by a second impedance sensor 416. If the first cell 410 is detected, the first push pump 438 frequency is halved, but the first pump 438 may continue to fire until the second cell 412 is detected by second impedance sensor 416. Similarly if a cell 412 is detected by the second impedance sensor 416 the second pump 440 frequency is halved, but the pumps 438 and 440 continue to fire until a cell is detected by the first impedance sensor 414. Once both cells are detected (e.g., by impedance sensor 414 and impedance sensor 416), the push pumps are stopped.

Once in their respective positions, the third fluid dispenser 424 fires, moving the two cells 410 and 412 together into the merging chamber 404. In the merging chamber 404, the electrodes 430 and 422 may be consistently turned on, with an AC electric field. When cells enter the merging chamber 404, the cells are porated and when they leave the electric field the merging chamber 404, fuse creating a fused cell, such as a hybridoma. Then, the third fluid dispenser 424 may be fired to move the fused cell through the merging chamber 404 and dispense it out of the microfluidic device. The fused cell may then be dispensed into a specific well of a microwell plate. The cells in the wells may be cultured, generating a monoculture of cells in each well. Thus, each well may produce a specific antibody, which can then be interrogated and selected for. Additionally, a waste collecting chamber 432 may be disposed orthogonal to the plane 442 and may collect waste fluid when the third fluid dispenser 424 is not firing.

Figure 6:
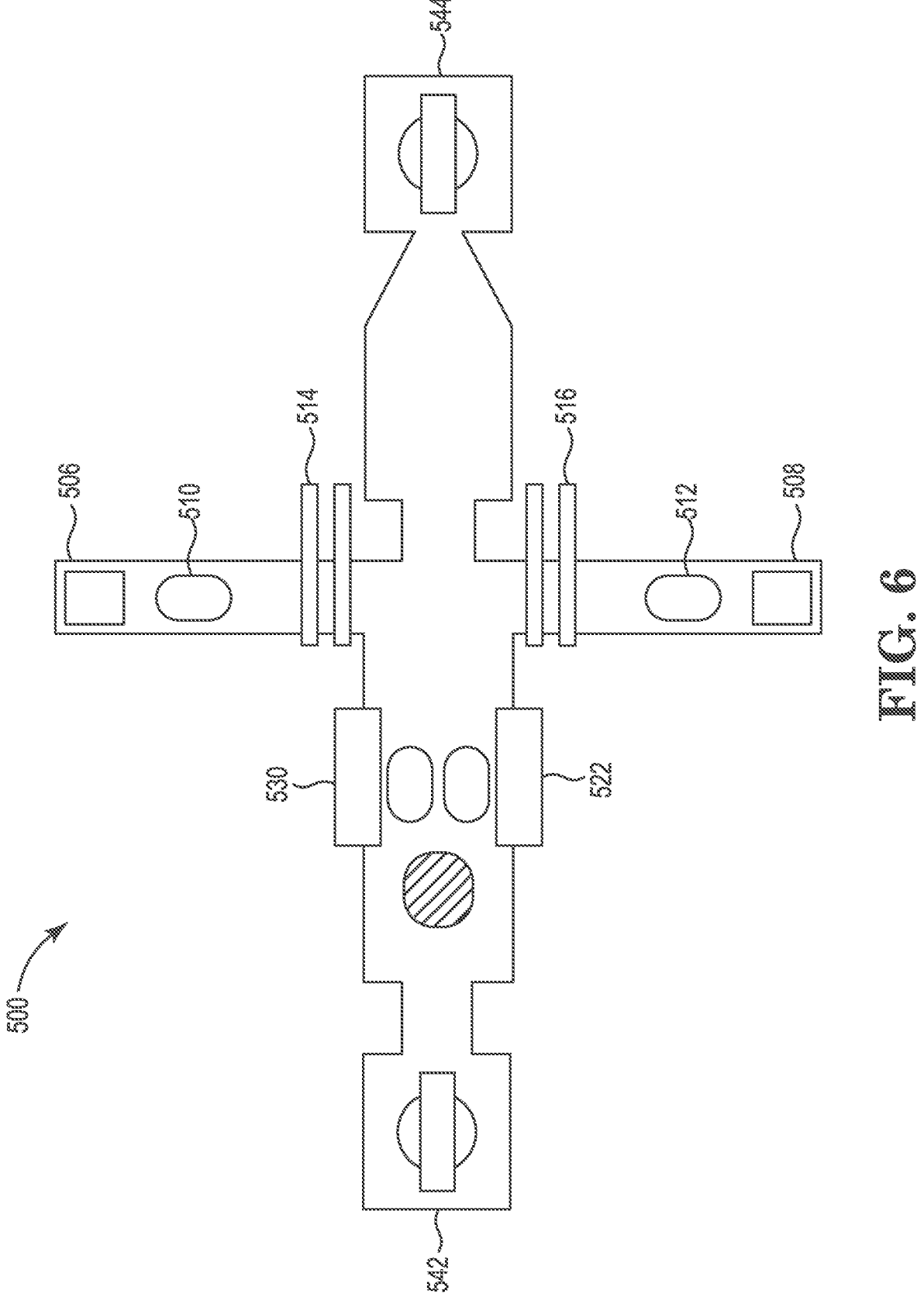
FIG. 6 illustrates an example apparatus with an orthogonal orientation and an additional fluid dispenser, in accordance with the present disclosure.

FIG. 6 illustrates an example apparatus 500 with an orthogonal orientation and an additional fluid dispenser, in accordance with the present disclosure. In general, the apparatus 500 shown in FIG. 4 may include various components that are the same and/or substantially similar to the apparatus 100 shown in FIG. 2, which was described in greater detail above. As such, for brevity and ease of description, various details relating to certain components in the apparatus 500 shown in FIG. 6 may be omitted herein to the extent that the same or similar details have already been provided above in relation to the apparatus 100 illustrated in FIG. 2. For instance, the apparatus 500 may include a first push pump 506, a second push pump 508, a first impedance sensor 514 and a second impedance sensor 516. A merging chamber including a first electrode 530 and a second electrode 522 may fuse cells 510 and 512, as described herein. Similarly, a third fluid dispenser 542 may dispense the fused cell, as discussed herein. As illustrated in FIG. 6, a fourth fluid dispenser 544 may be disposed opposite of the third fluid dispenser 542. The fourth fluid dispenser 544 may dispense waste or other fluids (other than the fused cell) into a well or other vessel.

Figure 7:
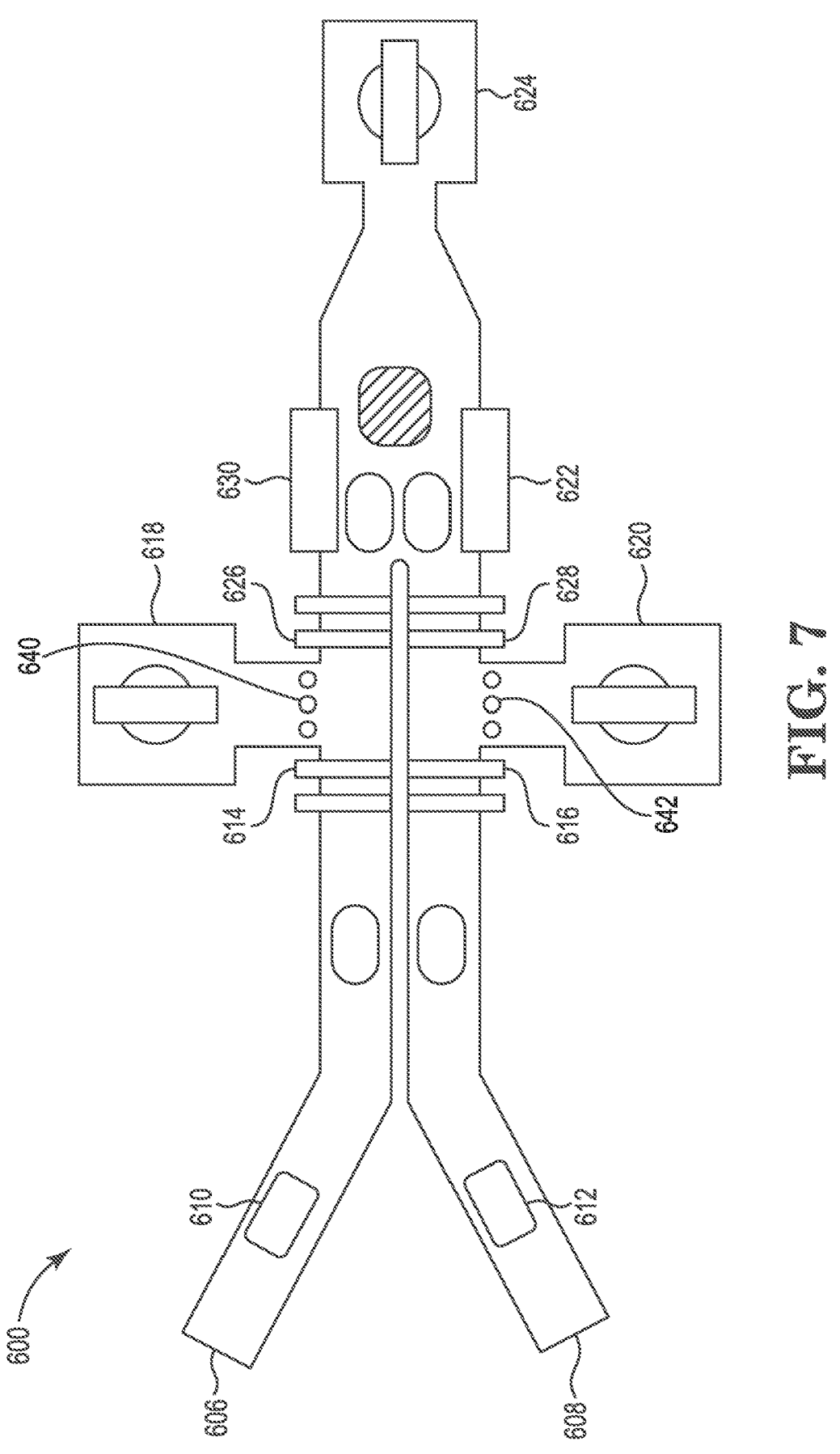
FIG. 7 illustrates an example apparatus including cell barriers, in accordance with the present disclosure.

FIG. 7 illustrates an example apparatus 600 including cell barriers, in accordance with the present disclosure. In general, the apparatus 600 shown in FIG. 7 may include various components that are the same and/or substantially similar to the apparatus 100 shown in FIG. 2, which was described in greater detail above. As such, for brevity and ease of description, various details relating to certain components in the apparatus 600 shown in FIG. 7 may be omitted herein to the extent that the same or similar details have already been provided above in relation to the apparatus 100 illustrated in FIG. 2. For instance, while cells 610 and 612, dispenser 624, dispenser 618, dispenser 620, electrode 622, and electrode 630 are illustrated in FIG. 7, details relating to cells 610 and 612, dispenser 624, dispenser 618, dispenser 620, electrode 622, and electrode 630 are not provided with reference to FIG. 7.

As illustrated in FIG. 7, a first plurality of barriers 640 may be used to prevent cells from escaping into the first fluid dispenser 618, and a second plurality of barriers 642 may be used to prevent cells from escaping into the second fluid dispenser 620. The plurality of barriers 640 and 642 maybe constructed from pillars, wires or other shapes to enable liquid flow, while not allowing cells to enter. Also as illustrated in FIG. 7, a first set of impedance sensors, 614 and

616 may be disposed on a first side of the plurality of barriers 640 and 642, and a second set of impedance sensors, 626 and 628, may be disposed on a second side of the plurality of barriers 640 and 642.

FIG. 8 illustrates an example apparatus 809 for alignment and fusion of cells with an electrical field, in accordance with the present disclosure. As illustrated in FIG. 8, the apparatus 809 may include a processor 811, and a computer-readable storage medium 813. The apparatus 809 may perform the method 10 illustrated in FIG. 1.

The processor 811 may be a central processing unit (CPU), a semiconductor-based microprocessor, and/or other hardware device suitable to control operations of the apparatus 809. Computer-readable storage medium 813 may be an electronic, magnetic, optical, or other physical storage device that contains or stores executable instructions. Thus, computer-readable storage medium 813 may be, for example, Random Access Memory (RAM), an Electrically Erasable Programmable Read-Only Memory (EEPROM), a storage device, an optical disc, etc. In some examples, the computer-readable storage medium 813 may be a non-transitory storage medium, where the term 'non-transitory' does not encompass transitory propagating signals. As described in detail below, the computer-readable storage medium 813 may be encoded with a series of executable instructions 815-819.

In some examples, computer-readable storage medium 813 includes instructions 815 that when executed, cause the apparatus 809 to align a first cell in a first microfluidic channel of an electrofusion device parallel with a second cell in a second microfluidic channel of the electrofusion device by firing a first fluid dispenser in the first microfluidic channel and a second fluid dispenser in the second microfluidic channel.

In some examples, the instructions 815 to align the first cell in the first microfluidic channel with the second cell in the second microfluidic channel, include instructions that, when executed, cause the processor 811 to change a firing rate of the first fluid dispenser in response to receipt of a first signal from a first impedance sensor in the first microfluidic channel indicative of the presence of the first cell. In some examples, the instructions 815 to align the first cell in the first microfluidic channel with the second cell in the second microfluidic channel, include instructions that, when executed, cause the processor 811 to move the first cell in the first microfluidic channel by firing the first fluid dispenser at a first firing rate, and move the second cell in the second microfluidic channel by firing the second fluid dispenser at a second firing rate.

The computer-readable storage medium 813 may further include instructions 817 that when executed, cause the apparatus 809 to fire a third fluid dispenser of the electrofusion device, in response to alignment of the first cell in the first microfluidic channel with the second cell in the second microfluidic channel.

The computer-readable storage medium 813 may further include instructions 819 that when executed, cause the apparatus 809 to fuse the first cell and the second cell in a merging chamber of the electrofusion device by creating an electrical field in the merging chamber.

In some examples, the computer-readable storage medium 813 includes instructions that when executed, cause the apparatus 809 to receive a first signal from a first impedance sensor in the first microfluidic channel indicative of the presence of the first cell, receive a second signal from a second impedance sensor in the second microfluidic channel indicative of the presence of the second cell, and stop firing the first fluid dispenser and the second fluid dispenser in response to receipt of the first signal and the second signal.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. An apparatus, comprising:

a pairing region, comprising:

a first microfluidic channel including a first impedance sensor, wherein the first microfluidic channel is in fluidic communication with a first fluid dispenser; and a second microfluidic channel including a second impedance sensor, wherein the second microfluidic channel is in fluidic communication with a second fluid dispenser;

a non-transitory computer readable medium storing instructions that, when executed:

actuate the first fluid dispenser to move a first cell within the first microfluidic channel and actuate the second fluid dispenser to move a second cell within the second microfluidic channel until the first cell in the first microfluidic channel is aligned with the second cell in the second microfluidic channel within the same plane such that neither the first cell nor the second cell is closer to a merging chamber than the other of the first cell or the second cell;

the merging chamber in fluid communication with the first microfluidic channel and the second microfluidic channel, wherein the merging chamber comprises a plurality of electrodes that, when activated, generate an electric field within the merging chamber, a third fluid dispenser fluidly coupled with the merging chamber at a side opposite a location at which the first microfluidic channel and the second microfluidic channel are coupled with the merging chamber, wherein the instructions, when executed:

actuate the third fluid dispenser to move both of the first cell and the second cell, while aligned, through the merging chamber to fuse the first cell with the second cell to generate a third cell in the electric field generated by the plurality of electrodes, in response to alignment of the first cell in the first microfluidic channel with the second cell in the second microfluidic channel.

2. The apparatus of claim 1, wherein the non-transitory computer readable medium includes instructions that, when executed, cause the first fluid dispenser to actuate until the first impedance sensor detects the first cell in the first microfluidic channel, and the second fluid dispenser to actuate until the second impedance sensor detects the second cell in the second microfluidic channel.

3. The apparatus of claim 1, wherein the non-transitory computer readable medium includes instructions that, when executed, cause the first fluid dispenser to actuate at a reduced rate responsive to the first impedance sensor detecting the first cell in the first microfluidic channel.

4. The apparatus of claim 1, wherein the first microfluidic channel and the second microfluidic channel are disposed in series with the merging chamber, and the first microfluidic channel and the second microfluidic channel are disposed in parallel.

5. The apparatus of claim 1, wherein the first fluid dispenser and the second fluid dispenser include resistors.

6. The apparatus of claim 1, wherein the first impedance sensor is disposed upstream from a first junction between the first microfluidic channel and the first fluid dispenser, and the second impedance sensor is disposed upstream from a second junction between the second microfluidic channel and the second fluid dispenser.

7. The apparatus of claim 6, further comprising a third impedance sensor disposed downstream from the first junction and a fourth impedance sensor disposed downstream from the second junction, wherein the third impedance sensor and the fourth impedance sensor are disposed upstream from the merging chamber.

* * * * *